(12) United States Patent
Strange et al.

(10) Patent No.: US 10,090,112 B2
(45) Date of Patent: *Oct. 2, 2018

(54) USE OF ETCH RESIST MASKED ANODE FRAME FOR FACILITATION OF LASER CUTTING, PARTICLE AND LEAKAGE CURRENT REDUCTION

(71) Applicant: Pacesetter, Inc., Sunnyvale, CA (US)

(72) Inventors: Thomas F. Strange, Easley, SC (US); Ralph Jason Hemphill, Sunset, SC (US); David R. Bowen, Taylors, SC (US); Kurt J. Erickson, Anderson, SC (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/996,456

(22) Filed: Jan. 15, 2016

(65) Prior Publication Data

US 2017/0207030 A1   Jul. 20, 2017

(51) Int. Cl.
| | |
|---|---|
| *H01G 9/042* | (2006.01) |
| *H01G 9/145* | (2006.01) |
| *H01G 9/055* | (2006.01) |
| *H01G 9/00* | (2006.01) |
| *A61N 1/39* | (2006.01) |
| *C23F 1/14* | (2006.01) |

(52) U.S. Cl.
CPC ........... *H01G 9/042* (2013.01); *A61N 1/3956* (2013.01); *C23F 1/14* (2013.01); *H01G 9/0029* (2013.01); *H01G 9/055* (2013.01); *H01G 9/145* (2013.01)

(58) Field of Classification Search
CPC .............. H01G 9/00; H01G 9/06; H01G 9/08
See application file for complete search history.

(56) References Cited

U.S. PATENT DOCUMENTS

| | | | |
|---|---|---|---|
| 3,622,843 A | 11/1971 | Vermiyea | |
| 3,779,877 A | 12/1973 | Alwitt | |
| 3,872,579 A | 3/1975 | Papadopoulos | |
| (Continued) | | | |

FOREIGN PATENT DOCUMENTS

| | | |
|---|---|---|
| JP | 59083772 A | 5/1984 |
| JP | 02075155 A | 3/1990 |
| (Continued) | | |

OTHER PUBLICATIONS

Non-Final Office Action dated Nov. 3, 2004; Related U.S. Appl. No. 10/680,777.

(Continued)

*Primary Examiner* — Seahvosh Nikmanesh
(74) *Attorney, Agent, or Firm* — Theresa A. Raymer

(57) ABSTRACT

The present invention is directed to a method of etching anode foil in a non-uniform manner which minimizes thermal oxidation during foil cutting. Having less oxide improves the ability to cut through aluminum anodes with lower energy rates. In aluminum foils, it has been found that a masking step before etching reduces conversion of boehmite aluminum oxide to alpha-phase corundum during laser cutting of anodes, which increases edge quality and productivity. Additionally, the non-etched anode frame allows for less surface area to form during the aging process. As a result, the leakage current is reduced by the proportion of edge to anode surface area, and the aging process will be faster, leading to higher productivity.

21 Claims, 3 Drawing Sheets

(56) References Cited

U.S. PATENT DOCUMENTS

| | | |
|---|---|---|
| 4,213,835 A | 7/1980 | Fickelscher |
| 4,266,332 A | 5/1981 | Markarian et al. |
| 4,420,367 A | 12/1983 | Locher |
| 4,474,657 A | 10/1984 | Arora |
| 4,481,084 A | 11/1984 | Chen et al. |
| 4,518,471 A | 5/1985 | Arora |
| 4,525,249 A | 6/1985 | Arora |
| 4,541,037 A | 9/1985 | Ross et al. |
| 4,593,343 A | 6/1986 | Ross |
| 4,663,824 A | 5/1987 | Kenmochi |
| 4,696,082 A | 9/1987 | Fonfia |
| 5,131,388 A | 7/1992 | Pless et al. |
| 5,175,227 A | 12/1992 | Gardon et al. |
| 5,230,962 A | 7/1993 | Stephenson |
| 5,522,841 A | 6/1996 | Roby et al. |
| 5,522,851 A | 6/1996 | Fayram |
| 5,602,198 A | 2/1997 | Das et al. |
| 5,660,737 A | 8/1997 | Elias et al. |
| 5,663,240 A | 9/1997 | Simeone et al. |
| 5,715,133 A | 2/1998 | Harrington et al. |
| 6,168,706 B1 | 1/2001 | Hemphill et al. |
| 6,224,738 B1 | 5/2001 | Sudduth et al. |
| 6,426,864 B1 | 7/2002 | O'Phelan |
| 6,686,124 B1 | 2/2004 | Angelopoulos et al. |
| 6,736,956 B1 | 5/2004 | Hemphill et al. |
| 6,802,954 B1 | 10/2004 | Hemphill et al. |
| 6,858,126 B1 | 2/2005 | Hemphill et al. |
| 7,452,473 B1 | 11/2008 | Hemphill et al. |
| 7,745,281 B2 | 6/2010 | Prymak et al. |
| 8,535,507 B1 | 9/2013 | Hemphill et al. |
| 8,734,964 B2 | 5/2014 | Kurihara et al. |
| 8,888,967 B2 | 11/2014 | Hemphill et al. |
| 9,275,800 B2 | 3/2016 | Ribble et al. |
| 9,412,525 B2 | 8/2016 | Bowen et al. |
| 9,852,849 B2 * | 12/2017 | Hemphill ............. H01G 9/0029 |
| 2002/0111029 A1 | 8/2002 | Johnson |
| 2014/0329140 A1 * | 11/2014 | Mikuni ................... C01B 33/26 429/188 |

FOREIGN PATENT DOCUMENTS

| | | |
|---|---|---|
| JP | 04056309 A | 2/1992 |
| JP | 07049428 A | 2/1995 |
| WO | 2000/19470 | 4/2000 |

OTHER PUBLICATIONS

"A New Coating Process for Aluminum" by Patel et al. Posted on Oct. 25, 2000 on http://www.ceramicindustry.com. Downloaded from http://www.ceramicindustry.com/CDA/ArticleInformation/Features/BNP_Features_Item/0,270,1364,00.html on Oct. 21, 2004.

Amendment filed Mar. 3, 2005: Related U.S. Appl. No. 10/680,777.

Final Office Action dated May 23, 2005; Related U.S. Appl. No. 10/680,777.

English translation of JP 059-083772 performed by USPTO Translator Akiko Smith.

Notice of Appeal dated Sep. 23, 2005; Related U.S. Appl. No. 10/680,777.

Amendment filed Sep. 23, 2005; Related U.S. Appl. No. 10/680,777.

Notice of Allowance dated Sep. 24, 2008; Related U.S. Appl. No. 10/940,793.

Amendment filed Aug. 28, 2008; Related U.S. Appl. No. 10/940,793.

Examiner Interview Summary dated Aug. 1, 2008; Related U.S. Appl. No. 10/940,793.

Amendment filed Jun. 30, 2008; Related U.S. Appl. No. 10/940,793.

Final Office Action dated Mar. 28, 2008; Related U.S. Appl. No. 10/940,793.

Amendment filed Jan. 7, 2008; Related U.S. Appl. No. 10/940,793.

Non-Final Office Action dated Oct. 5, 2007; Related U.S. Appl. No. 10/940,793.

Amendment filed Sep. 21, 2007; Related U.S. Appl. No. 10/940,793.

Final Office Action dated Jun. 21, 2007; Related U.S. Appl. No. 10/940,793.

Amendment filed Apr. 10, 2007; Related U.S. Appl. No. 10/940,793.

Non-Final Office Action dated Jan. 10, 2007; Related U.S. Appl. No. 10/940,793.

* cited by examiner

USE OF ETCH RESIST MASKED ANODE FRAME FOR FACILITATION OF LASER CUTTING, PARTICLE AND LEAKAGE CURRENT REDUCTION

BACKGROUND OF THE INVENTION

Field of the Invention

The present invention is directed to a method of etching anodic foil for use in the manufacture of electrolytic capacitors and more particularly, to a method of etching of anode foil to produce higher capacitance foil with improved leakage current and deformation, and to an electrolytic capacitor incorporating the etched anode foil of the present invention for use in an implantable cardioverter defibrillator (ICD).

Related Art

Compact, high voltage capacitors are utilized as energy storage reservoirs in many applications, including implantable medical devices. These capacitors are required to have a high energy density since it is desirable to minimize the overall size of the implanted device. This is particularly true of an Implantable Cardioverter Defibrillator (ICD), also referred to as an implantable defibrillator, since the high voltage capacitors used to deliver the defibrillation pulse can occupy as much as one third of the ICD volume.

Implantable Cardioverter Defibrillators, such as those disclosed in U.S. Pat. No. 5,131,388, incorporated herein by reference, typically use two electrolytic capacitors in series to achieve the desired high voltage for shock delivery. For example, an implantable cardioverter defibrillator may utilize two 350 to 400 volt electrolytic capacitors in series to achieve a voltage of 700 to 800 volts.

Electrolytic capacitors are used in ICDs because they have the most nearly ideal properties in terms of size, reliability and ability to withstand relatively high voltage. Conventionally, such electrolytic capacitors include an etched aluminum foil anode, an aluminum foil or film cathode, and an interposed kraft paper or fabric gauze separator impregnated with a solvent-based liquid electrolyte. While aluminum is the preferred metal for the anode plates, other metals such as tantalum, magnesium, titanium, niobium, zirconium and zinc may be used. A typical solvent-based liquid electrolyte may be a mixture of a weak acid and a salt of a weak acid, preferably a salt of the weak acid employed, in a polyhydroxy alcohol solvent. The electrolytic or ion-producing component of the electrolyte is the salt that is dissolved in the solvent. The entire laminate is rolled up into the form of a substantially cylindrical body, or wound roll, that is held together with adhesive tape and is encased, with the aid of suitable insulation, in an aluminum tube or canister. Connections to the anode and the cathode are made via tabs. Alternative flat constructions for aluminum electrolytic capacitors are also known, comprising a planar, layered, stack structure of electrode materials with separators interposed therebetween, such as those disclosed in the above-mentioned U.S. Pat. No. 5,131,388.

In ICDs, as in other applications where space is a critical design element, it is desirable to use capacitors with the greatest possible capacitance per unit volume. Since the capacitance of an electrolytic capacitor increases with the surface area of its electrodes, increasing the surface area of the anode foil results in increased capacitance per unit volume of the electrolytic capacitor. By electrolytically etching an anode foil, an enlargement of a surface area of the foil will occur. Electrolytic capacitors which are manufactured with such etched foils can obtain a given capacity with a smaller volume than an electrolytic capacitor which utilizes a foil with an unetched surface.

In a conventional electrolytic etching process, surface area of the foil is increased by electrochemically removing portions of the foil to create etch tunnels. For example, U.S. Pat. Nos. 4,474,657, 4,518,471 and 4,525,249 to Arora disclose the etching of aluminum electrolytic capacitor foil by passing the foil through an electrolyte bath. The preferred bath contains 3% hydrochloric acid and 1% aluminum as aluminum chloride. The etching is carried out under a direct current (DC) and at a temperature of 75° C. U.S. Pat. No. 4,474,657 is limited to the above single step. U.S. Pat. No. 4,518,471 adds a second step where the etched foil is treated in a similar bath with a lower current density and at a temperature of 80-82.5° C. U.S. Pat. No. 4,525,249 adds a different second step, where the etched foil is treated in a bath of 8% nitric acid and 2.6% aluminum as a nitrate, at a temperature of 85° C.

The ideal etching structure is a pure tunnel-like etch with defined and uniform tunnel diameters and without any undesirable pitting of the foil. As tunnel density (i.e., the number of tunnels per square centimeter) is increased, a corresponding enlargement of the overall surface area will occur. Larger surface area results in higher overall capacitance. However, as tunnel density increases more of the aluminum foil is removed, reducing the strength of the remaining foil. Therefore a compromise must be made between foil strength and capacitance gain.

Traditionally, electrolytic capacitor foil is etched uniformly over the surface. With a uniform, random tunnel etch, the useable capacitance gain of the anode foil is limited by the strength requirements of the foil in its particular application. Thus, there is a need in the art for an etch process which increases the overall capacitance of the foil while retaining foil strength.

U.S. Pat. No. 5,660,737 to Elias et al. ("the Elias patent") discloses a process providing an etch mask to cover during the etch process those portions of the anode foil which will be subjected to stress during the construction of the capacitor.

U.S. Pat. No. 6,736,956 to Hemphill et al. ("the Hemphill patent") discloses applying a mechanical grid to an etched foil to protect regions of the foil from further etching. The process of the Hemphill patent results in a web of lightly etched or unetched anode foil surrounding areas of more highly etched anode foil.

SUMMARY OF THE INVENTION

One aspect of the present invention is directed to a method of etching anode foil in a non-uniform manner which increases the overall capacitance of the foil while retaining foil strength. The foil perimeter is masked and not etched; masking the foil improves leakage current and deformation, eliminates friable edge, reduces conversion of boehmite aluminum oxide to alpha phase corundum, and retains foil strength.

In particular, by using a mask to protect regions of the foil from etching, a foil can be etched prior to the widening step. The higher surface area in the exposed areas does not significantly decrease the strength of the foil as a whole.

In one embodiment, an etch-resistant mask is applied to an aluminum anode foil prior to etching of the foil. The mask defines a frame or perimeter that is protected from etching and exposes unmasked areas for etching. The mask may be applied by inkjet printing, lithography, photolithography, or other suitable means. The mask itself may be comprised of an acrylic ink, poly(4-hydroxystyrene), copolymers of 4-hydroxystyrene, novolac resins, fluorocarbon polymers, cycloaliphatic polymers, polyurethane polyols, polyesterurethanes, and cross-linked variants and copolymers and mixtures and thereof. Next, the foil is placed in an etch electrolyte solution and etched. The mask is applied in such a way that the etched/exposed area does not create large scale strength defects such as perforation holes and can be applied in any shape desired, such that the exposed area perimeter can be round, square, hexagonal, triangular, or any other shape and size. After widening and forming, a foil etched according to the present invention is suitable for use as an anode in an electrolytic capacitor. The cut anode foil will have minimized alpha-phase boehmite oxide corundum and enhanced capacitance without increased brittleness, which could render the foil unusable or sub-optimal. Additional aspects of the invention are directed to such anodes and electrolytic capacitors.

BRIEF DESCRIPTION OF THE FIGURES

The foregoing and other features and advantages of the invention will be apparent from the following, more particular description of a preferred embodiment of the invention, as illustrated in the accompanying drawings.

DETAILED DESCRIPTION OF THE PREFERRED EMBODIMENTS

Figure 1:
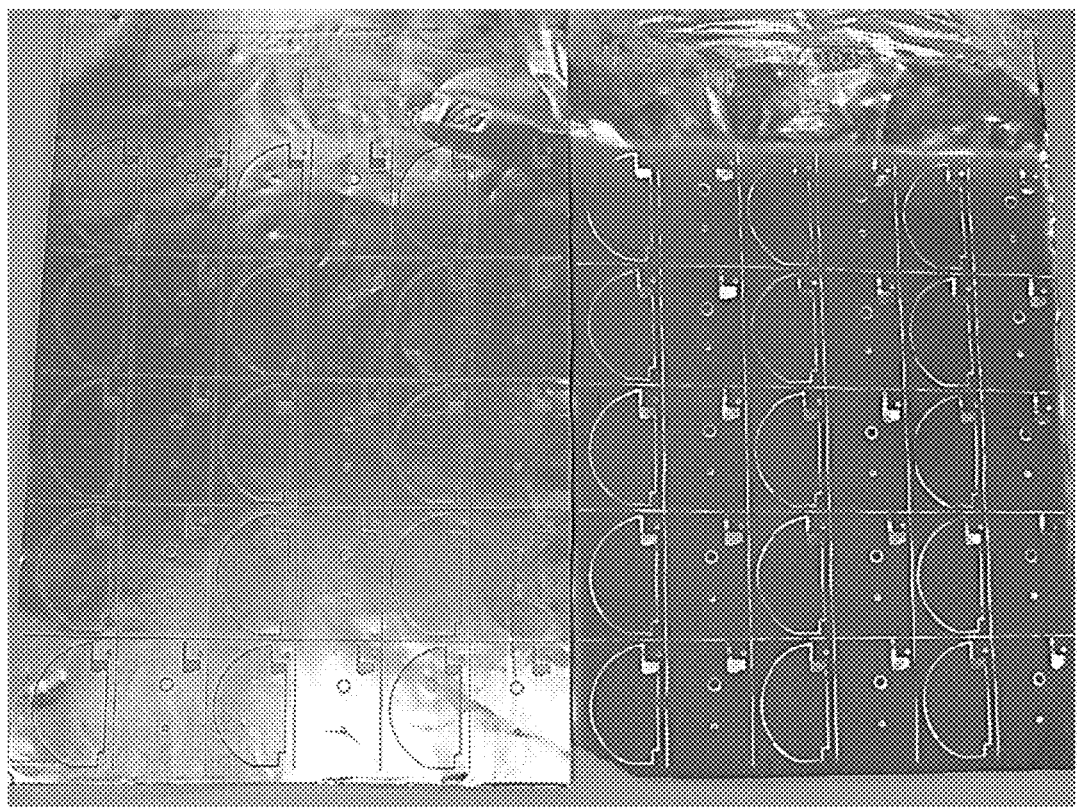
FIG. 1 shows a picture of a foil etched according to the present invention.

One aspect of the invention is directed to a process for etching an aluminum foil to minimize thermal oxidation and produce higher capacitance foil without sacrificing foil strength, to a process for creating an aluminum anode foil, and to an etched aluminum anode foil etched by such processes for use in an implantable cardioverter defibrillator (ICD).

Embodiments of the invention are now described. While specific configurations and arrangements are discussed, it should be understood that this is done for illustrative purposes only. A person skilled in the relevant art will recognize that other configurations and arrangements can be used without departing from the spirit and scope of the invention. It will be apparent to a person skilled in the relevant art that this invention can also be employed in a variety of other devices and applications.

According to the present invention, an anode metal foil to be etched is selected. Aluminum foil is preferred, because of its ability to produce a sufficient quality oxide layer, its conductive properties, and its wide commercial availability. However, other foils conventionally utilized in electrolytic capacitors could also be used, including tantalum, magnesium, titanium, niobium, zirconium and zinc. Preferably, a 100 to 125 micron thick, unetched, high purity (at least 99.98%) strip of aluminum foil with high cubicity, wherein at least 80% the crystalline aluminum structure is oriented in a normal position (i.e., a (1,0,0) orientation) relative to the surface of the foil, is used. Such foils are well-known in the art and are readily available from commercial sources.

Initially, an etch-resistant mask is applied to a metal foil, such as aluminum foil. Application of the mask defines an unmasked or exposed area and a masked frame or perimeter. Application of the mask protects the frame or perimeter from being etched and leaves the unmasked area exposed for etching. The resulting non-etched frame allows for less oxide formation due to less surface area on the edges of the anodes. Having less oxide improves the ability to cut thorough the aluminum foils, to form etched anode foils, with lower energy rates, or lower heating. Additionally, the non-etched frame or perimeter allows for less surface area to form during the aging process, or less surface area to convert to alpha-phase oxide. Conversion of boehmite aluminum oxide to alpha-phase corundum has been found to cause the leakage current to increase by 100 to 200% and to increase deformation by at least 50 times. Reducing corundum formation allows laser cutting of anodes, which increases edge quality and productivity. Therefore, the leakage current will be reduced by the proportion of edge to anode surface. Additionally, the aging process will be faster leading to higher productivity. The frames can be created of various geometries to completely mask the frame or create slight hazy frame. The frame can be applied to both sides or faces of the foil or only one side or face.

The etch-resistant mask may be applied by any suitable means known to persons of skill in the art. In some embodiments, the mask is applied using inkjet printing, lithography, or photolithography. Preferably, the mask is applied using inkjet printing. In some embodiments, the mask is cured optically without solvent. In some embodiments, the mask is cured using ultraviolet light.

The etch-resistant mask may be comprised of any suitable material or materials that resist etching in the etch electrolyte composition used. In some embodiments, the etch-resistant mask comprises an acrylic ink, poly(4-hydroxystyrene), copolymers of 4-hydroxystyrene, novolac resins, fluorocarbon polymers, cycloaliphatic polymers, polyurethane polyols, polyesterurethanes, and cross-linked variants and copolymers and mixtures and thereof. Preferably, the mask comprises an acrylic ink.

Next, the aluminum foil is placed in an etch electrolyte solution and etched, according to a conventional etch process, as known to those skilled in the relevant art, to produce an enlargement of surface area of at least 20 times. Surface area of the foil is increased by electrochemically removing portions of the foil to create etch tunnels, as disclosed in U.S. Pat. Nos. 4,474,657, 4,518,471, 4,525,249 and 5,715,133. Since the capacitance of an electrolytic capacitor increases with the surface area of its electrodes, increasing the surface area of the anode foil results in increased capacitance per unit volume of the electrolytic capacitor. By electrolytically etching an anode foil, an enlargement of a surface area of the foil will occur. Electrolytic capacitors which are manufactured with such etched foils can obtain a given capacity with a smaller volume than an electrolytic capacitor which utilizes a foil with an unetched surface. In a preferred embodiment, the aluminum foil is etched in a high temperature etch electrolyte that is based on a halide and/or oxyhalide, preferably a chloride and/or oxychloride, and contains an oxidizer such as peroxide, persulfate, cerium sulfate or sodium periodate, at a pH of 0.0 to 8.0, preferably a pH of 1.0 to 3.0. Other surface area enhancing etch solutions can be used with the present invention to produce similar results. In the preferred embodiment, the electrolyte etch solution consists of 0.1% to 10% NaCl, preferably 1.3% NaCl, and 0.1% to 10% $NaClO_4$, preferably 3.5% $NaClO_4$. The electrolyte is heated to a temperature of 80° C. to 100° C., with a preferred temperature of 85° C. The foil is placed in the etch electrolyte and etched at a current density of 0.1 to 0.3 amps/cm$^2$, preferably 0.15 amps/cm$^2$, and at an etch charge of 5 to 50 Coulombs/cm$^2$ for a specific amount of time, preferably 36 Coulombs/cm$^2$ for 4 minutes.

The pattern is configured in such a way that the enhanced area does not create large scale strength defects such as perforation holes, divots, chunk removal and the like, and can be applied in any size or shape desired, such as round, square, hexagonal, triangular, or any other shape, that will produce the desired results of the present invention. The preferred pattern according to the present invention is one that allows the capacitance gain to be enhanced, while the strength is maintained. The mask and pattern are chosen to optimize the etch area as compared to the masked area to achieve the full benefit of the present invention.

Next, the foil may be rinsed in an overflow deionized water bath for a time of 1 to 10 minutes, preferably 1.5 minutes.

After the etching step, the etch-resistant mask is removed using chemical means or treatment in an oven to burn the etch-resistant mask away. The specific conditions to remove the etch-resistant mask can be any suitable conditions to remove the mask without damaging the anode foil. In embodiments where the mask comprises acrylic ink, the mask may be removed using ethyl lactate. In some embodiments, the mask is removed using chemical means, using a solvent that does not react with aluminum or aluminum oxide under the conditions used.

The foil is then widened in a chloride or nitrate containing electrolyte solution known to those skilled in the art, such as that disclosed in U.S. Pat. Nos. 3,779,877 and 4,525,249. Then the foil is dipped into a deionized water bath at a temperature of 80° C. to 100° C., preferably 95° C. to form a hydrate later on the foil surface.

Next, a barrier oxide layer may be electrochemically formed onto one or both surfaces of the metal foil, sufficiently thick to support the intended use voltage, by placing the foil into a forming solution, including but not restricted to a solution based on azelaic acid, sebacic acid, suberic acid, adipic acid, dodecanedioic acid, citric acid or other related organic acids and salts, preferably a citric acid solution at a temperature of 80° C. to 100° C., preferably 85° C., at a current density of 1 mA/cm$^2$ to 40 mA/cm$^2$, preferably 16 mA/cm$^2$. A formation voltage of 50 to 800 Volts, preferably 490 V, can be applied to the foil to form the barrier oxide layer. The barrier oxide layer provides a high resistance to current passing between the electrolyte and the metal foils, also referred to as the leakage current. A high leakage current can result in the poor performance and reliability of an electrolytic capacitor. In particular, a high leakage current results in greater amount of charge leaking out of the capacitor once it has been charged.

A heat treatment of 500° C.±20° C. may be applied to the foil following formation for 1 to 10 minutes, preferably 4 minutes. The foil is then returned to the forming solution and allowed to soak with no applied potential for 1 to 10 minutes, preferably 2 minutes. A second formation in the same electrolytic forming solution at high temperature is performed at a potential of 480 Volts.

Next, the foils are dipped in a suitable low concentration oxide-dissolving acid solution including but not restricted to phosphoric acid, formic acid, acetic acid, citric acid, oxalic acid, and acids of the halides, preferably phosphoric acid, a concentration of 1% to 10%, preferably a concentration of 2%, at a temperature of 60° C. to 90° C., preferably 70° C., for an time of 1 to 10 minutes, preferably 4 minutes.

Next, the foils are reformed at a voltage of 480 Volts in a suitable forming solution, as discussed above, at a high temperature, preferably 80° C. to 100° C., more preferably 85° C.

Finally, the foil is cut along the unetched perimeter or frame, to form an etched foil anode. The conditions for cutting the anode foils can be any suitable conditions known to persons of skill in the art. In some embodiments, the foil is laser cut. Suitable conditions are those which achieve an ablative threshold for the material and then limit the heat input and provide a good atmosphere for the nascent surfaces and finishing off with debris removal. In some embodiments, it is desirable to maintain as low an energy as possible to cut the foil while minimizing the heating effect.

Anode foils etched according to the present invention have less thermal oxide formation along the frame than foils cut without a masking step. Thermal oxidation in the anode foils of the present invention is reduced. In certain embodiments, thermal oxidation is reduced by greater than 90%, or by greater than 92%, or by greater than 95%, or by greater than 97%, or by greater than 98%, or by greater than 99%. Anode foils etched according to the present invention will also have enhanced capacitance without the increased brittleness, which would render such foil unusable, typical of anode foils highly etched according to conventional methods. Foils that are processed according to the present invention can be utilized for a variety of applications that require a high capacitance foil. For example, as discussed above, high capacitance anode foils are widely utilized in electrolytic capacitors. Electrolytic capacitors comprising anode foils manufactured according to the present invention exhibit improved leakage current compared to capacitors manufactured with anode foils etched by a process not using a masking step. Electrolytic capacitors, which are manufactured with anode foils etched according to the present invention, can obtain a given capacity with a smaller volume than currently available electrolytic capacitors and, therefore, can be very compact in size.

Electrolytic capacitors manufactured with anode foils etched according to the present invention can be utilized in ICDs, such as those described in U.S. Pat. No. 5,522,851 to Fayram, incorporated by reference herein in its entirety, such that the improved leakage current of the electrolytic capacitor allows for a reduction in the size of the ICD.

Having now generally described the invention, the same will be more readily understood through reference to the following examples which are provided by way of illustration, and are not intended to be limiting of the present invention.

EXAMPLES

Example 1

FIG. 1 demonstrates one example of minimizing the masked surface area. The picture on the left depicts a foil printed with Circuit Jet 200 with a solid frame mask (completely masked) on one side only alternating front to back. The foils without a frame mask in the picture have a frame mask on the back. Alternately, a masked frame may be applied to both sides. The picture on the right shows the foil after it has been etched, the etch resist has been removed, and the foil has been widened and formed as described above. The edges are fully masked on one side and alternate front to back from position to position.

Example 2

Figure 2:
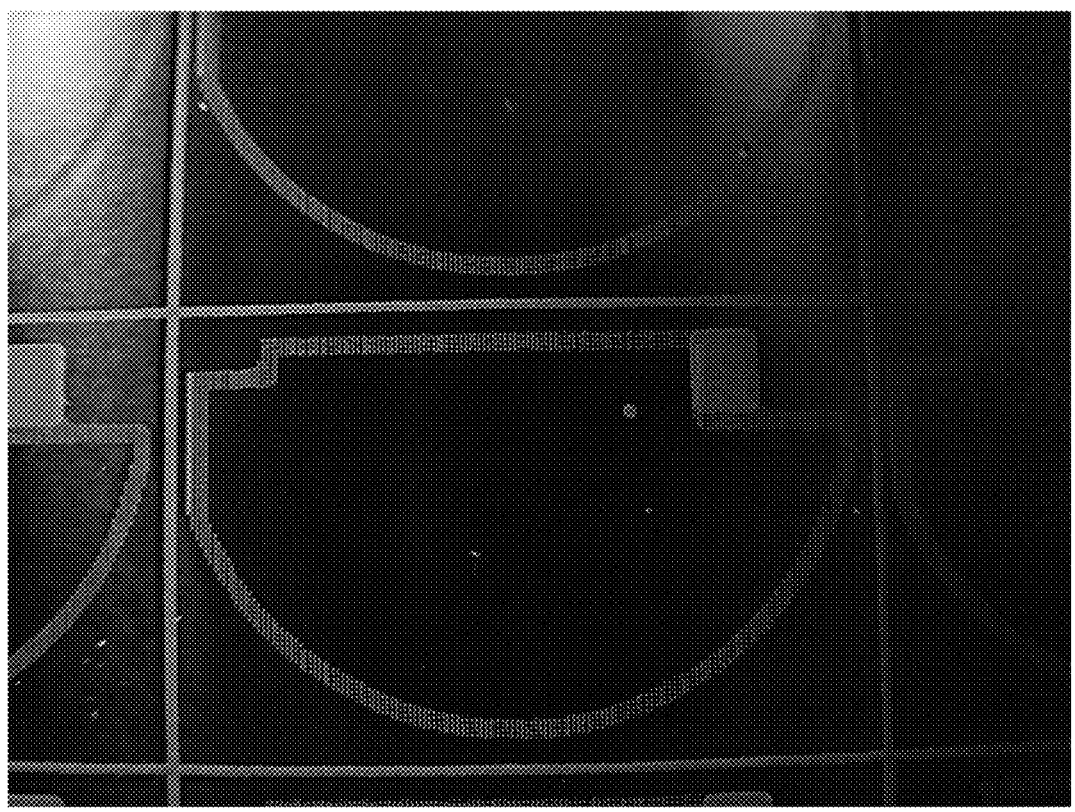
FIG. 2 shows a picture of etch-resistant mask around the edge of the anode masked according to the present invention.
Figure 3:
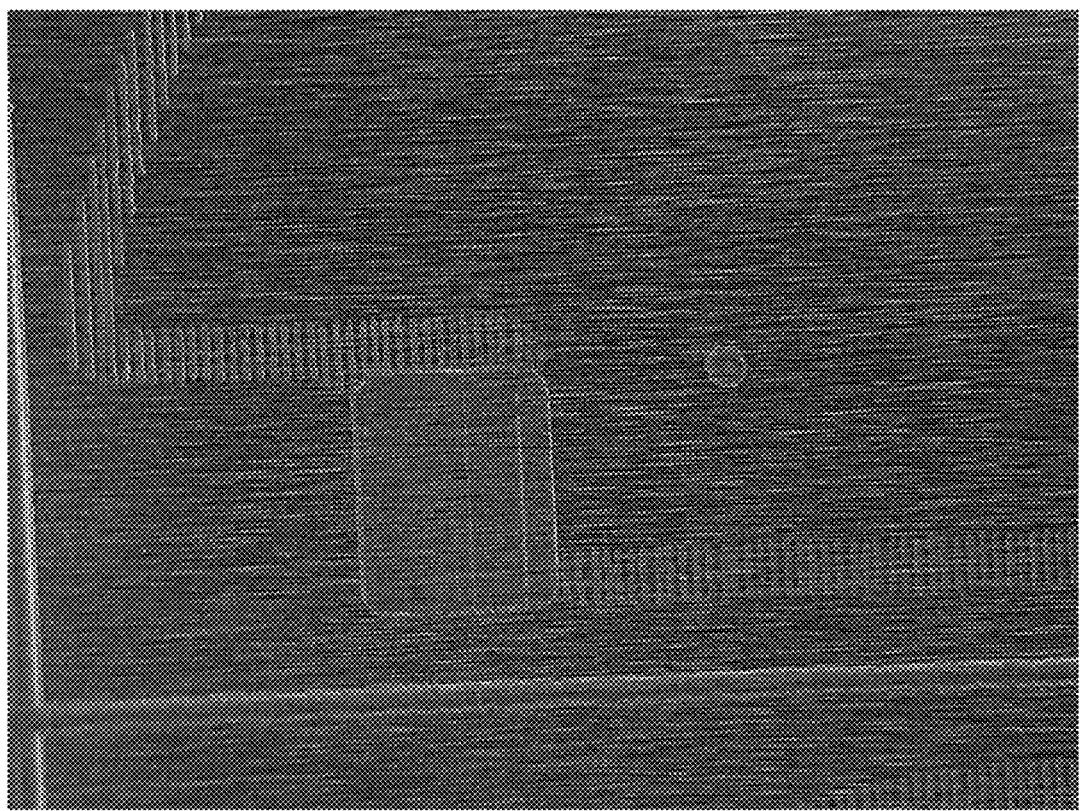
FIG. 3 shows a close-up of FIG. 2.

FIG. 2 shows a close-up of a frame printed mask that is not a solid line. The print line is alternated leaving a 0.01-inch gap between each 0.01-inch line print. FIG. 3 shows a more close up view of the alternating line gaps.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents. Additionally, all references cited herein, including journal articles or abstracts, published or corresponding U.S. or foreign patent applications, issued U.S. or foreign patents, or any other references, are each entirely incorporated by reference herein, including all data, tables, figures, and text presented in the cited references.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A process for etching a metal foil, comprising:
   depositing an etch-resistant mask upon predetermined portions of a metal foil to define a perimeter of an anode;
   placing the masked metal foil in an etch electrolyte solution;
   etching said masked metal foil, such that the exposed area is etched; and
   removing the etch-resistant mask, wherein removing the mask leaves an unetched perimeter.

2. The process of claim 1, further comprising the step of cutting the metal foil along the unetched perimeter, to form an etched foil anode.

3. The process of claim 1, wherein the etch-resistant mask is selected from the group consisting of an acrylic ink, poly(4-hydroxystyrene), copolymers of 4-hydroxystyrene, novolac resins, fluorocarbon polymers, cycloaliphatic polymers, polyurethane polyols, polyesterurethanes, and cross-linked variants and copolymers and mixtures thereof.

4. The process of claim 1, wherein the etch-resistant mask is deposited using inkjet printing, lithography, or photolithography.

5. The process of claim 1, wherein the metal foil is an aluminum foil.

6. A process for creating a metal anode foil, comprising:
   depositing an etch-resistant mask directly upon predetermined portions of the metal foil, thereby defining an anode perimeter;
   placing the masked metal foil in an etch electrolyte solution;
   etching said masked metal foil, such that the exposed area is etched;
   removing the etch-resistant mask, wherein removing the etch-resistant mask leaves an unetched perimeter;
   widening;
   forming; and
   cutting the foil along the unetched perimeter, to form an etched foil anode;
   wherein the cut foil has less thermal oxide formation along the perimeter than a foil cut without masking.

7. The process of claim 6, wherein the etch-resistant mask is selected from the group consisting of an acrylic ink, poly(4-hydroxystyrene), copolymers of 4-hydroxystyrene, novolac resins, fluorocarbon polymers, cycloaliphatic polymers, polyurethane polyols, polyesterurethanes, and cross-linked variants and copolymers and mixtures thereof.

8. The process of claim 7, wherein the etch-resistant mask comprises an acrylic ink.

9. The process of claim 6, wherein the etch-resistant mask is deposited using inkjet printing, lithography, or photolithography.

10. The process of claim 9, wherein the etch-resistant mask is deposited using inkjet printing.

11. A process for creating a metal anode foil, comprising:
    applying an etch-resistant mask to predetermined portions of a metal foil to define an anode perimeter;
    placing the masked metal foil in an etch electrolyte solution;
    etching said masked metal foil, such that the exposed area is etched;
    removing the etch-resistant mask, wherein removing the etch-resistant mask leaves an unetched perimeter;
    widening;
    forming; and
    cutting the foil along the unetched perimeter, to form an etched foil anode;
    wherein the cut foil has less thermal oxide formation along the perimeter than a foil cut without masking,
    wherein thermal oxidation of the anode foil is reduced by greater than 99%.

12. A process for etching a metal foil, comprising:
    applying an etch-resistant mask to predetermined portions of a metal foil to define a perimeter of an anode;
    placing the masked metal foil in an etch electrolyte solution;
    etching said masked metal foil, such that the exposed area is etched; and
    removing the etch-resistant mask, wherein removing the mask leaves an unetched perimeter,
    wherein thermal oxidation of the etched, masked metal foil is reduced by greater than 99% than a foil etched without masking.

13. The process of claim 1, wherein the etch-resistant mask is deposited upon an unetched surface of the metal foil.

14. The process of claim 6, wherein the etch-resistant mask is deposited directly upon an unetched surface of the metal foil.

15. The process of claim 1, further comprising the step of curing the mask.

16. The process of claim 1, wherein removing the etch-resistant mask comprises removing the etch-resistant mask using chemical means.

17. The process of claim 1, wherein removing the etch-resistant mask comprises removing the etch-resistant mask using ethyl lactate.

18. The process of claim 1, wherein removing the etch-resistant mask comprises removing the etch-resistant mask using an oven to burn the etch-resistant mask away.

19. The process of claim 1, wherein depositing the etch-resistant mask upon the predetermined portions of the metal foil to define the perimeter of the anode comprises printing a line having alternating line gaps on the metal foil.

20. The process of claim 1, wherein depositing the etch-resistant mask upon the predetermined portions of the metal foil to define the perimeter of the anode comprises printing an etch-resistant mask on the metal foil.

21. The process of claim 1, wherein depositing the etch-resistant mask upon the predetermined portions of the metal foil to define the perimeter of the anode comprises depositing the etch-resistant mask such as to form the mask directly upon the predetermined portions of the metal foil such as to define the perimeter of the anode prior to etching the foil.

* * * * *